United States Patent [19]

Dafoe

[11] 4,416,660
[45] Nov. 22, 1983

[54] METHOD OF TRANSVAGINAL STERILIZATION

[76] Inventor: Charles A. Dafoe, 725 Republic Bldg., Denver, Colo. 80202

[21] Appl. No.: 902,159

[22] Filed: May 2, 1978

Related U.S. Application Data

[63] Continuation of Ser. No. 594,269, Jul. 9, 1975, Pat. No. 4,136,695.

[51] Int. Cl.³ ............................................. A61M 1/00
[52] U.S. Cl. ............................................................ 604/55
[58] Field of Search .............. 128/1 R, 235, 215, 216, 128/218 R, 218 N, 236, 221, 260, 130; 604/54, 55, 49

[56] References Cited

U.S. PATENT DOCUMENTS

| | | | |
|---|---|---|---|
| 2,700,385 | 1/1955 | Ortiz | 128/215 |
| 2,740,404 | 4/1956 | Kohl | 128/215 |
| 2,923,295 | 2/1960 | Guerriero | 128/215 |
| 3,739,780 | 6/1973 | Ogle | 128/221 |
| 3,822,702 | 7/1974 | Bolduc et al. | 128/235 |

OTHER PUBLICATIONS

Dafoe et al., (Dafoe), "Chemical Occlusion at the Uterotubal Junction in Monkeys," *American Journal of Obstetrics and Gynecology*, vol. 113, No. 3, pp. 388–393, Jun. 1, 1972.

"Transvaginal Delivery of Sterilizing Chemicals" by Thompson et al., Human Sterilization, 1972.

*Primary Examiner*—John D. Yasko
*Attorney, Agent, or Firm*—John E. Reilly

[57] ABSTRACT

A method for sterilization of females has been devised in which one or more hypodermic needles can be inserted into the uterus to a predetermined position or location at the uterine cornu and the internal tubal ostra followed by injecting a sclerosing agent which produces a chronic lesion at that point. The entire needle assembly is characterized by slidable mounting of the needle or needles within a guide or sleeve projecting forwardly from a disposable cartridge, and a hand-held actuator is provided to selectively control successive advancement of each needle through the needle guide into the tissue and advancement of the ampule or cartridge to force the sclerosing agent or other medicament through the needle. Thereafter, the needle assembly may either be withdrawn or relocated to another position for injection of medicament through the same or other needle advancing through the same needle guide into the opposite cornul portion.

3 Claims, 11 Drawing Figures

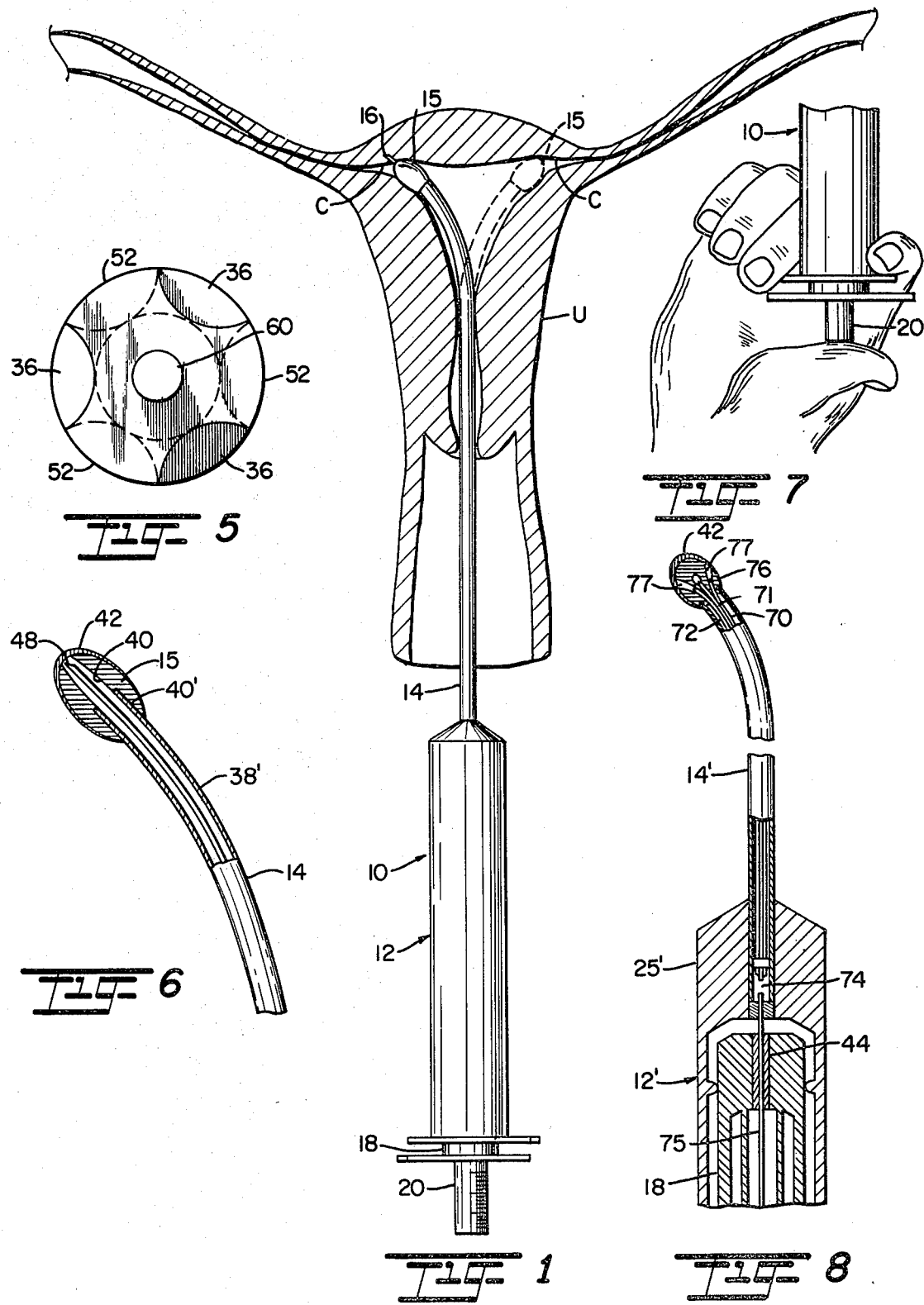

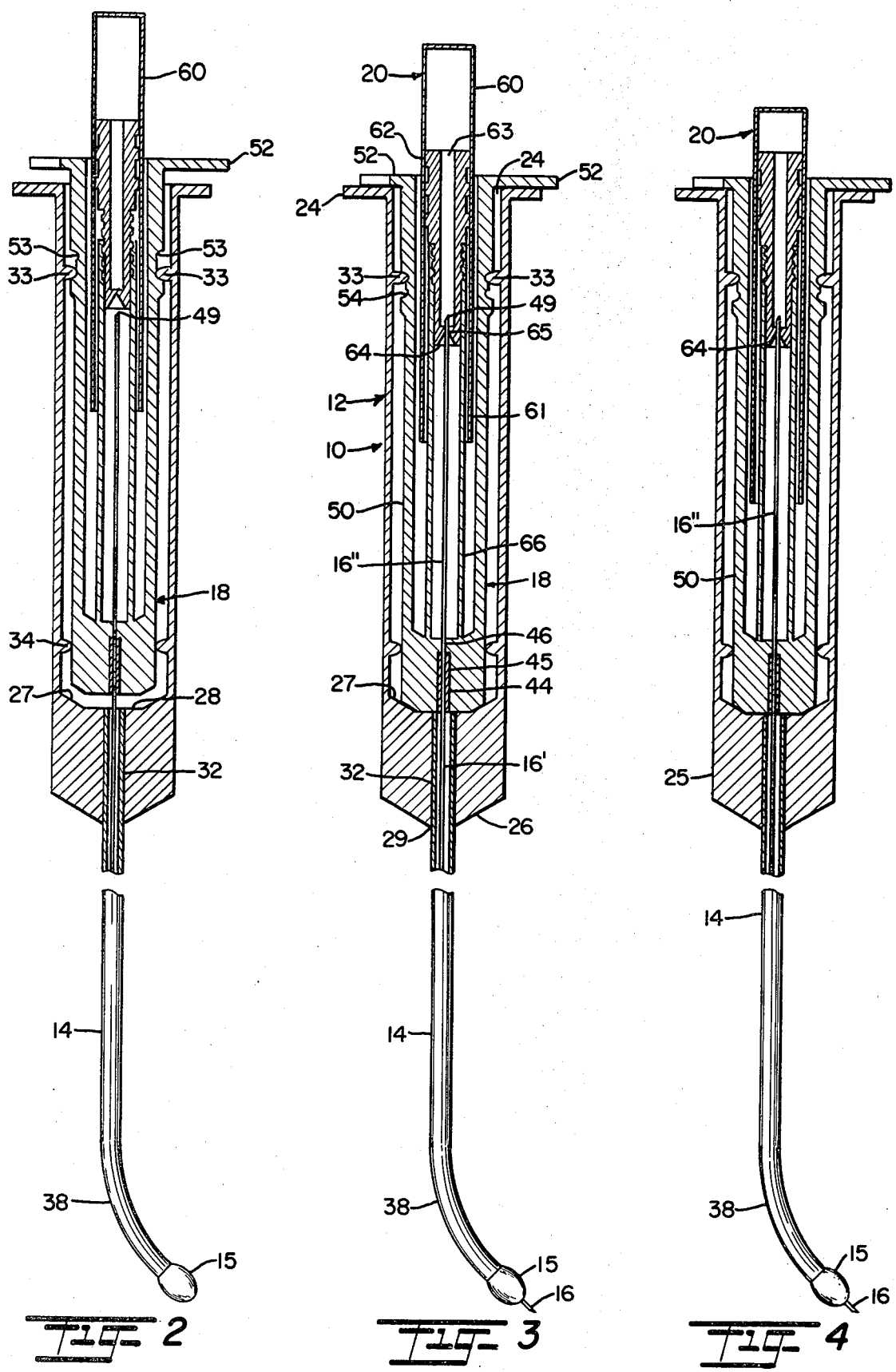

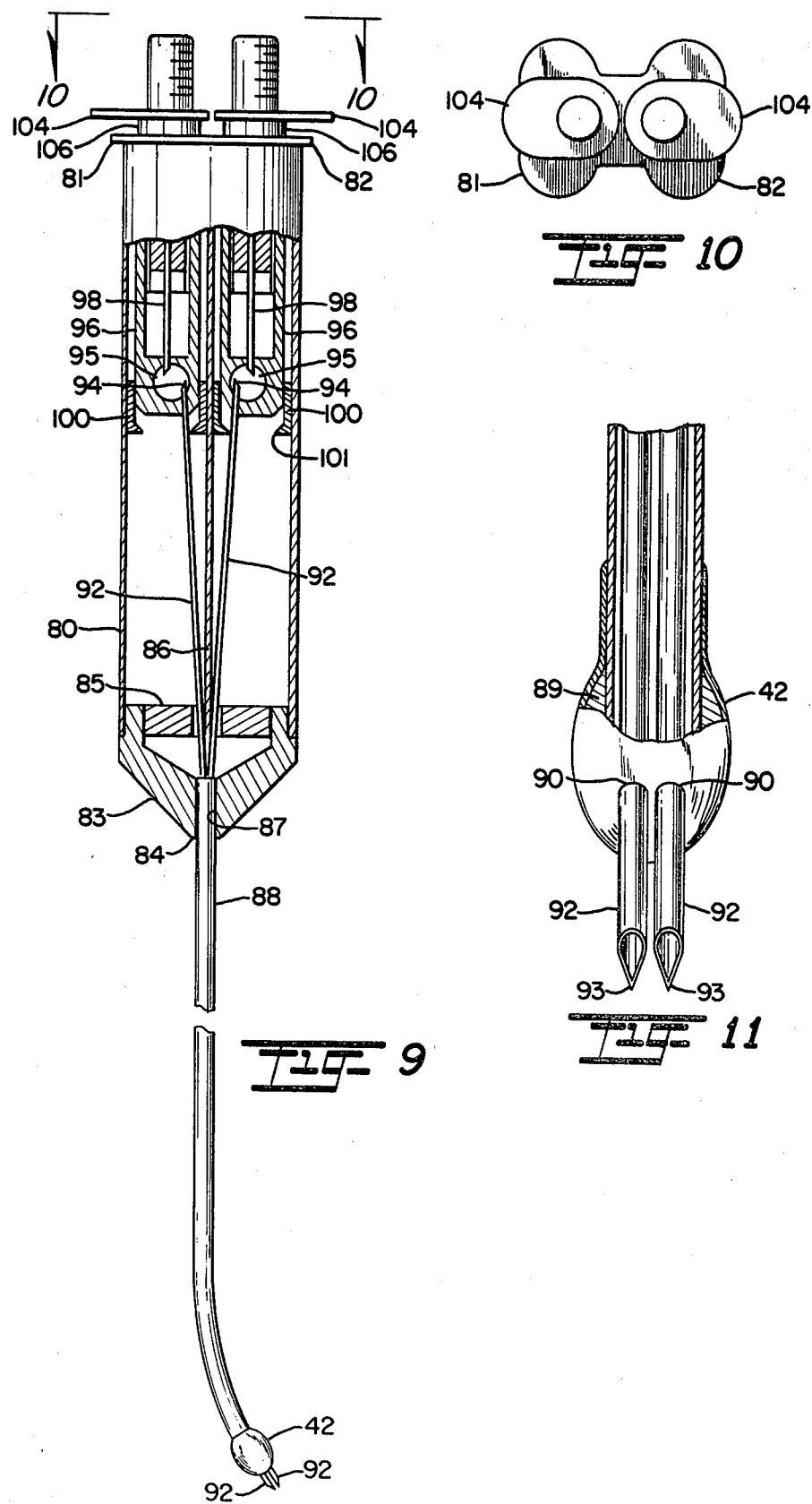

METHOD OF TRANSVAGINAL STERILIZATION

This is a continuation application of Ser. No. 594,269, filed July 9, 1975 now U.S. Pat. No. 4,136,695, and entitled *TRANSVAGINAL STERILIZATION INSTRUMENT AND METHOD OF STERILIZATION.*

BACKGROUND OF THE INVENTION

This invention relates to a novel and improved method for the blind injection of medical solutions into one or more predetermined locations within a cavity of the body; and more particularly relates to a novel method for occluding the fallopian tubes for sterilization of females in a rapid, safe and efficient manner.

Various methods and techniques have been devised and utilized over the years for sterilization or birth control of females. Innumerable types of contraceptives have been suggested and utilized as a temporary means of birth control but have never been found to be completely effective. Similarly, although certain drugs have been found to be an effective means of temporary sterilization or birth control, side effects of these drugs is at best uncertain. In any case, none of the temporary means of sterilization or birth control proposed is capable of providing longterm sterilization and requires either regular use or dosages in order to be effective. Of course, surgical procedures are in use which will achieve permanent sterilization but in most all cases cannot be resorted to as a means of longterm temporary sterilization or birth control.

It is well known that a common cause of sterility is the blockage of the Fallopian tubes by inflammation, and it follows that an ideal method of sterilization would be the transvaginal introduction of an inflammatory agent which would occlude the cornul portion of the tubal lumen, since at this location in female mammals there is found a narrow canal on opposite sides of the uterus which is surrounded by dense and highly tonic uterine muscles resembling a sphincter. The principal difficulties inherent in this approach to sterilization are not only the utilization of an inflammatory agent which will reliably produce the necessary occlusion but in the method and instrumentation of introducing the agent in a blind fashion so as to assure in each case that the injection is made at precisely the proper location without pain or injury to the patient. Moreover, it is highly desirable that the inflammatory agent be injected on both sides of the uterus.

Studies conducted to date have demonstrated the ability to inject under direct vision into the uterine cornus of certain female mammals a sclerosing agent which would produce scarring in animal tissue, i.e., a chronic lesion over fairly extended time periods. Here, reference is made to my earlier publications jointly with other authors which describe earlier work done in the field of female sterilization; "Transvaginal Delivery of Sterilizing Chemicals" *Human Sterilization,* (1972); "Chemical Occlusion at the Uterotubal Junction in Monkeys," *American Journal of Obtetrics Gynec.,* (1972); "Evaluation of Experimental Methods of Occluding the Uterotubal Junction," *Female Sterilization* (1972). In the selection of a sclerosing agent, particularly good results were realized through the use of paraformaldehyde or polyoxymethylene adminstered in an alcohol solution and injected into the uterine wall in the region of the Fallopian tubes ostra. Specifically, the results of more recent testing with the use of paraformaldehyde solutions revealed longterm sterilization for periods as great as six weeks with little or no apparent side effects, and made apparent the desirability for a safe, reliable method and instrument for bilateral injection of the solution at precise locations in the uterus without benefit of visibility or physical touch and solely by manipulation and control of the instrument externally of the vagina.

SUMMARY OF THE INVENTION

It is therefore an object of the present invention to provide for a novel and improved method for sterilization of females which is safe and dependable in use and is capable of achieving long-term but temporary sterilization in a simplified, rapid and efficient manner.

It is another object of the present invention to provide for a novel and improved hypodermic needle assembly which will assure accurate positioning and guidance of a hypodermic needle into position for the blind injection of an inflammatory agent at the cornul portion of the tubal lumen; and a needle assembly which is capable of bilateral, blind injection of an inflammatory or sclerosing agent into the cornul portion on opposite sides of the uterus.

It is a further object of the present invention to provide for a hand-held hypodermic needle assembly which can be easily manipulated with one hand for insertion of the needle into position internally of the uterus, penetration of the needle into the tissue, injection of the inflammatory agent through the needle, and withdrawal of the needle from the tissue, followed by a repetition of the same sequence of steps on the opposite side of the uterus without removal of the entire needle guide assembly for repositioning or relocation of the needle.

It is another object of the present invention to provide for a hypodermic needle assembly which facilitates positioning and selective extension of one or more needles and injection of selected quantities of an inflammatory agent into different selected locations in the uterus in carrying out female sterilization procedures; and further wherein the hypodermic needle can be composed at least in part of disposable elements which are so constructed as to prevent contamination of the needle or accidental introduction of air into the needle guide when the needle is injected into the tissue.

It is a still further object to provide in a hypodermic needle assembly for a novel and improved means for selective manipulation of one or more needles and disposable cartridges in such a way that the assembly can be grasped with one hand and simultaneously manipulated with the other hand; and further wherein the needle assembly is lightweight, composed of a minimum number of parts and facilitates grasping and handling with a minimum number of operations required for the insertion, penetration of the needle and injection of the sclerosing agent.

In accordance with the present invention, long-term sterilization is achieved by the blind injection into the uterus of a sclerosing agent at the cornul portion of the tubal lumen on opposite sides of the uterus. The preferred method by which the same is accomplished comprises the steps of inserting a hypodermic needle assembly into the uterus with a needle guide disposed for extension at a predetermined angle to the longitudinal axis of the assembly, the guide being of a predetermined length and attitude so as to move safely into contact with the cornul portion without danger of injury to the wall or lining of the uterus. Upon insertion of the needle guide, one or more needles may be selectively advanced through a rupturable film which normally closes the end of the guide to penetrate the tissue at the cornul portion, followed by injecting a sclerosing agent through the needle to produce a chronic lesion at that point and consequent blockage of the fallopian tubes. Upon injection of the agent, the needle is withdrawn from the tissue and the needle guide turned or rotated into engagement with the cornul portion on the opposite side of the uterus and the foregoing procedure of penetration of the needle and injection of the agent repeated. The entire procedure can be carried out by a needle assembly which not only assures accurate placement of the needle guide and needle without benefit of visibility or touch but also permits holding and manipulation of the needle and syringe with one hand so as to leave the other hand completely free to steady and hold the needle assembly in place.

In the construction of the hypodermic needle assembly, one or more needles can be selectively advanced through the needle guide either for simultaneous or successive penetration into the body tissue. In the one modified form of invention, a double needle assembly has been devised in which each needle is disposed for independent advancement through a common needle guide and each needle is operatively associated with a separate syringe or cartridge for injection of the sclerosing agent through that needle. The double needle enables use of a separate needle and cartridge for each cornul portion without removal of the entire assembly from the uterus. In still another modified form of invention, a tri-needle assembly has been devised in which three needles are simultaneously advanced to penetrate an enlarged area of the cornul portion followed by injection of the agent from a single cartridge simultaneously through the three needles.

Additional features of the needle assembly in clude mounting and disposition of single or plural needles in the needle guide as well as the cooperative disposition of one or more disposable cartridges in a common housing. A unique form of finger-engaging needle support and guide are provided to greatly facilitate handling and manipulation of the needles while assuring that the needles remain in position as the sclerosing agent is injected therethrough into the tissue. The entire assembly except for the needle can be constructed of lightweight plastic material requiring a minimum number of parts which are well balanced and easy to manipulate in use. In addition, the assembly facilitates the use of a cartridge of the piston/cylinder type which enables operation and control with one hand.

The above and other objects, advantages and features of the present invention will become more readily appreciated and understood from a consideration of the following description when taken together with the accompanying drawings in which:

BRIEF DESCRIPTION OF THE DRAWINGS

FIG. 1 is a view of one form of hypodermic needle assembly illustrating successive placement of the needle guide within the uterus in carrying out the method of the present invention;

FIG. 2 is a view partially in section illustrating the form of needle guide assembly shown in FIG. 1 with the needle and cartridge in a retracted position;

FIG. 3 is a view partially in section of the first form of hypodermic needle assembly in which the needle is advanced forwardly through the needle guide for penetration into the body tissue;

FIG. 4 is still another illustration partially in section illustrating advancement of the syringe or cartridge with respect to the needle in order to inject an agent through the needle into body tissue;

FIG. 5 is an end view of the first form of hypodermic needle assembly shown in FIGS. 1 to 4;

FIG. 6 is an enlarged view partially in section of the needle guide and tip;

FIG. 7 is a somewhat perspective showing of the manipulation of the hypodermic needle assembly in carrying out the method of the present invention;

FIG. 8 is a cross-sectional view of a modified form of hypodermic needle assembly employing a tri-needle arrangement within a common needle guide;

FIG. 9 is a cross-sectional view of still another modified form of needle assembly in accordance with the present invention showing utilization of a pair of needles and associated syringes within a common housing and needle guide in accordance with the present invention;

FIG. 10 is an end view of the needle guide assembly illustrated in FIG. 9; and

FIG. 11 is an enlarged fragmentary view partially in section of the needle guide and tip in the modified form of FIG. 9.

DETAILED DESCRIPTION OF THE PREFERRED EMBODIMENT

Referring in more detail to the drawings, a first embodiment of the present invention is illustrated in FIGS. 1 to 7 and specifically illustrates a hypodermic needle assembly 10 comprising an outer housing 12, a needle guide 14 having a front generally rounded tip 15, a needle 16 adapted for extension through the needle guide, a needle support 18, and a disposable syringe or cartridge 20.

As a setting for the present invention, the needle assembly 12 is shown in FIG. 1 in inserted position within the uterus as generally designated at U and the cornul portion designated at C of a female mammal, the tip 15 being illustrated in full in contacting relation to the cornul portion C of the tubal lumen on one side of the uterus. The needle guide is further illustrated in dotted form when its position is reversed and the tip is brought into contact with the opposite side of the uterus. In carrying out the method of the present invention, transcervical tubal occlusion is achieved by the bilateral injection of a sclerosing agent into the cornul portions of the tubal lumen on opposite sides of the uterus. In order to produce a chronic lesion at the cornul portions, a preferred form of sclerosing agent is a sixteen molar suspension of paraformaldehyde in alcohol. Paraformaldehyde or polyoxymethylene is a solid, long chain polymerization of the aldehyde methanal. It has a chemical formula of $(CH_2O)_n$ and a molecular weight of $(30.03)_n$ and is preferably administered in a suspension of absolute ethanol ($C_2H_5OH$, M.W. 46.07) which can be injected into the uterine wall in the region of the fallopian tube ostia without producing undesirable side effects. Molar suspensions of paraformaldehyde in absolute ethanol are prepared in 10 ml. portions. For a sixteen molar suspension, 4.8078 grams of paraformaldehyde are added to the ten ml. of ethanol. The molar concentration possibly could vary between twenty molar and ten molar depending upon optimal effects of the human uterus. In preparations for monkeys, sixteen molar was found to be the optimal concentration. Most desirably a high grade paraformaldehyde is used such as the "Baker Grade" sold by the J. T. Baker Chemical Company.

The paraformaldehyde solution is placed in a disposable cartridge 20 and as a preliminary to insertion of the needle guide assembly into the uterus, the position of the uterus is determined by a bi-manual examination and a bivalve speculum inserted into the vagina. The cervix is washed with aqueous zepherin solution and a tanaculum placed in the anterior lip of the cervix. The cervix may be probed with a uterine sound to determine patency. Following this, the needle guide is inserted and advanced until the tip reaches the cornul portion. The needle is then advanced on the order of five millimeters and 0.5 cc of the sclerosing solution injected slowly over a fifteen second period of time. The needle is then withdrawn into the needle guide, the guide rotated or reversed to the opposite side of the uterus and the same procedure repeated without removing the needle guide from the uterine cavity.

Considering in more detail the construction and arrangement of the form of needle assembly shown in FIGS. 1 to 7, the housing 12 is of thin-walled, elongated hollow cylindrical configuration being open at its rearward end 24 and having a closed forward end 25. The forward end 25 terminates in a beveled end portion or nose 26, the end being thick-walled and provided with an inner inclined wall surface 27 and a flat central surface portion 28 disposed normal or perpendicular to the longitudinal axis of the housing. A guide passage 29 extends axially through the forward end 25 of the housing for the purpose of anchoring rearward end 32 of the needle guide 14. The inner wall surface of the housing 12 includes axially spaced, annular ribs 33 and 34, the uppermost rib 33 being located adjacent to the rearward open end 24 and the lower rib 34 being located adjacent to and just rearwardly of the inner inclined surface 27 of the forward end 25. In addition, finger-engaging lobes or flange portions 36 are arranged at equally spaced circumferential intervals around the rearward end 24 of the housing, there being a series of three lobes or flange portions 36 extending radially outwardly from the wall of the housing as illustrated in FIG. 5 to facilitate grasping of the end of the outer housing.

The needle guide 14 serves as a means of guiding forward extension of the needle 16 in a predetermined direction laterally away from the longitudinal axis of the needle assembly. For this purpose, the needle guide is comprised of a thin-walled, substantially rigid tubular portion having its rearward end 32 permanently affixed within the guide passage 29 of the front end of the housing and having a forward end 38 which undergoes a gradual bending or curvature away from the longitudinal axis at an angle approximating 10°–15°. The tip 15 of the needle guide is in the form of a bulbous or rounded, relatively thick-walled sleeve having a central bore 40 of a diameter corresponding to the inner diameter of the needle guide 14, and the diameter of the bore 40 is increased as at 40' to permit snug-fitting insertion of the forward end 38 of the needle guide 14 into the tip 15. The rounded tip 15 is securely bonded to the end of the needle guide so as to be integrally united thereto with the bore 40 forming a continuation of the forward end 38. In addition, a coating 42 which is in the form of a plastic sheath or covering covers the end of the tip 15 so as to seal the bore 40 against entry of body secretions when the needle guide is inserted and also serves to prevent loss of the alcohol from the sclerosing agent prior to penetration of the needle into the body tissue; otherwise, when the solution-filled needle is in contact with the uterine contents, because absolute ethanol alcohol is a dehydrating agent, as soon as it comes into direct contact with blood and fluid in the uterine cavity, it is drawn out of the needle leaving only a precipitate of paraformaldehyde crystal plugging the needle. Coating of the tip with a plastic film which will occlude the needle aperture at the distal end of the probe avoids this problem; and when the probe is fixed in the cornu the needle may be advanced through the film and into the muscle and the suspension or sclerosing agent injected without delay.

As shown in FIGS. 2 to 4, the needle 16 is conventionally constructed of a thin-walled, tubular hypodermic needle composed of stainless steel or similar material of the desired gauge, the needle being of a length to extend through the major length of the housing 12 and through the needle guide 14, and an intermediate portion 44 is fixed within a sleeve 45 which is mounted within a central bore 46 in the needle support 18. The forward section 16' of the needle projecting forwardly of the sleeve 45 is of a length such that when the needle support 18 is in a retracted or raised position as shown in FIG. 2 the pointed end 48 of the needle is aligned with the forward extremity of the tip 15; and when the needle support member is advanced forwardly into abutment with the inner surface of the front end 25 of the housing, the forward pointed end of the needle will advance beyond the tip for a distance of five millimeters so as to safely penetrate the body tissue and muscle at the cornul portion. The needle also includes a rearward extension 16" which extends rearwardly from the forward end of the needle support and extends for the greater length of the housing so as to terminate in a pointed end 49 normally spaced in front of the end of the disposable cartridge 20.

The needle support 18 serves to control axial advancement of the needle through the needle guide 14 as well as to lock the needle in its retracted and extended positions. To this end, the needle support 18 includes a hollow cylindrical portion 50 extending rearwardly from the front end of the needle support in spaced inner concentric relation to the housing 12 and terminates at its rearward end in spaced, radially outwardly projecting, finger-engaging lobes 52. The finger-engaging lobes or flange portions 52 are so aligned with respect to the lobes 36 on the housing as to be evenly spaced therebetween; and as shown in FIG. 5 are arranged at equally spaced circumferential intervals between the lobes 36. The needle support is centered with respect to the housing by means of the ribs 33 and 34 on the housing wall; and the external surface of the cylindrical wall 50 is provided with axially spaced annular grooves 53 and 54, the groove 53 receiving the rib 33 in order to lock the needle in its advanced position projecting from the tip, and the groove 54 receiving the rib 33 in order to lock the needle in its retracted position. Movement of the needle between its retracted and advanced positions is of course controlled by manipulation of the finger-engaging lobes 52 and facilitates grasping of the underside of the lobes 36 between the thumb and middle fingers while pressing down on the lobes 52 with the forefinger to urge the needle forwardly through the needle guide until the rib 33 is locked in place in the rearwardmost groove 53.

The disposable cartridge 20 may be of conventional construction and as illustrated in FIGS. 2 to 4 is of the piston/cylinder type having an outer vial or ampule 60 which contains the liquid medicine and a grooved plunger 62 provided with a hollow bore 63 opening at its rearward end into the vial and closed as at 64 at its opposite forward end. The forward end 64 includes a centrally located diaphragm 65 which is easily ruptured by the pointed end 49 of the needle when the cartridge is advanced forwardly through the needle support 18. The cartridge is guided in its forward advancement by a hollow cylindrical guide portion 66 directed rearwardly from the inner surface of the front end of the needle support in inner spaced concentric relation to the outer wall 50 and to the cylindrical wall 61 of the cartridge 20 and which threadedly engages the external surface of the plunger 62. The construction of the cartridge is conventional and for example may be of the type manufactured and sold by Bristol Laboratories of Syracuse, N.Y., under the trademark "Abboject Syringe," Model No. NDC 0074-4916-01 except that the dimensioning and configuration are modified and reduced for interworking with the needle support and housing. In this relation, the disposable cartridge is readily installed by inserting the plunger within the cylindrical wall 66 and threading into position. Thereafter, forward advancement of the cartridge by depressing the vial 60 will cause the pointed end of the needle 49 to rupture the diaphragm 65 and to move into liquid communication with the interior of the plunger 62. Continued advancement of the vial will force the liquid within the vial through the central bore 63 in the plunger and through the interior of the needle for injection into the tissue. The external surface of the cartridge 20 is provided with suitable graduations to measure the amount of agent injected in accordance with conventional practice. The cartridge 20 may readily be replaced by unthreading the plunger from the wall support 66 and replacing with a new cartridge, although it will be apparent that the entire needle assembly may be comprised of disposable elements and normally would not be designed for repeated use.

In the modified form of needle assembly illustrated in FIG. 8, like parts are correspondingly enumerated, the modification residing in a series of three needles 70, 71 and 72 arranged for slidable extension through the needle guide 14, the needles 70-72 terminating at their rearward end in a common manifold 74 which is affixed to the forward end of a single needle section 75 extending through the needle support 18 and affixed to the needle support at 44. The manifold 74 establishes liquid communication between the rearward needle section 75 and the forward needles 70-72, and at the same time defines a coupling between the needle section with the rearward needle section having its forward end firmly anchored in one end of the manifold 74 and the needle sections 70-72 having their rearward ends firmly anchored in the opposite or forward end of the manifold. The guide passage 29' in the front end 25' of housing 12' is slightly enlarged to accommodate a greater size or diameter of needle guide 14', but in other respects the construction of the housing 12' corresponds to that described in the first form shown in FIGS. 1 to 7. Similarly, the needle support 18 corresponds to the needle support shown in the first form.

The needles 70 to 72 each terminate in a front pointed end disposed in apertures 77 in the rounded tip 76. The rounded tip 76 at the end of the needle guide 14' differs from the tip 15 of the first form in that separate guide passages or apertures 77 are formed at equally spaced circumferential intervals branching or radiating out at a slight angle from the front extremity of the needle guide so as to function as guide channels for forward divergent movement of the pointed ends of the needle through the tip in penetrating into the skin. The angle of divergence between the apertures or guide channels 77 is very slight, preferably being on the order of less than 5° with respect to the axis of the needle guide but sufficient to insure spacing between the pointed ends of the needles in penetrating the body tissue. In this way, when the sclerosing agent is injected through the needles it is disseminated over a wider area to assure a greater region of scarring or lesion at the cornul portion. However, the total quantity of sclerosing agent injected corresponds to that previously described.

In the other modified form of invention shown in FIGS. 9 to 11, a double needle assembly is illustrated. However, its intended use and function differs from that of the tri-needle concept described with respect to FIG. 8 in that each needle is equipped with a separate cartridge or supply of sclerosing agent and each is adapted to be independently activated so that a separate needle can be used for injection into each cornul portion without necessity of removing the needle assembly from the uterus. In the modified form of invention as shown, an outer housing takes the form of a hollow thin-walled casing 80 of generally oval-shaped, cross-sectional configuration having radially outwardly extending flange portions 81 and 82 at opposite ends of the major axis of rearward open end of the casing. The casing may be of uniform cross-section throughout its length and at its forward end has an end cap 83 provided with a forwardly tapered nose 84 and a guide ring 85 mounted at the rearward end of the end cap adjacent to its point of attachment to the forward end of the housing. The housing is divided into two separate symmetrical chambers by a central wall or divider 86 extending the substantial length of the housing and tapering forwardly so as to terminate at its forward end in inner spaced concentric relation to the needle guide ring 85. The end cap 83 includes an axially extending guide passage 87 to receive the rearward end of needle guide 88 which is permanently affixed such as by bonding to the wall of the guide passage and terminates at its forward extremity in a tip 89 having a pair of laterally spaced apertures or guide channels 90 in communication with the interior of the needle guide. A pair of needles 92 are disposed for slidable extension through the needle guide and terminate in front pointed ends 93. In turn, rear pointed ends 94 diverge rearwardly through the casing and each extends into chamber 95 formed at the forward or leading end of a needle support portion 96. Each needle support 96 is of hollow generally cylindrical configuration, except for its leading end, and contains an axially extending needle section 98 in liquid communication with the chamber 95 and in offset relation to the rearward extremity 94 of each needle 92, the rearward needle section 98 extending rearwardly along the longitudinal axis of each respective needle support. Each needle support 96 is slidably disposed within a retainer ring 100 on each side of the divider 86, each ring 100 terminating at its front end in an inwardly protruding annular rim or lip 101 so as to limit forward movement of the needle support 96. An external rib 97 on each needle support is slidable within a longitudinal slot 99 in the guide ring 100 to limit outward movement of the needle support with respect to the housing. The rearward open end of each needle support has a radially outwardly projecting, finger-engaging tab 104 projecting beyond the outer edge of the lobes 81.

Each of the needle supports 96 is designed internally in the same manner as the first form of needle support described with reference to FIGS. 1 to 7 for the purpose of receiving a conventional form of disposable cartridge 106 through its rearward open end. In the manner previously described with reference to FIGS. 1 to 7, each disposable cartridge is slidably disposed in axial alignment with a rearward needle section 98, and upon depression of the cartridge will cause the needle section to rupture the diaphragm at the leading end of the cartridge to establish communication with the interior of the cartridge vial.

In operation, after first inserting the needle assembly in place, one of the needles is activated by depressing one of the needle supports 96 to cause forward advancement of the needle tip 93 through the tip of the needle guide 88. The cartridge 106 associated with that needle support is then depressed to rupture its diaphragm and by continued inward forcing cause a selected amount of sclerosing agent to be injected through the associated needle. The needle is then withdrawn or retracted by lifting up the finger-engaging tab 104 and repositioning the needle assembly into alignment with the opposite cornul portion. The other needle is then advanced and the sclerosing agent injected through the needle into the other cornul portion and the entire assembly removed. Again a plastic film or covering 42 is applied over the end of the tip 89 to prevent accidental loss of the alcohol in the sclerosing agent as earlier described.

From the foregoing, it will be appreciated that a unique method and means have been devised for female sterilization which permits blind, accurate injection of a sclerosing agent into the cornul portions of the uterus and consequent blockage of the fallopian tubes. The length and curvature of the needle guide in each case is such as to assure accurate placement of the assembly without injury to the uterine wall and while assuring smooth advancement of the needle into the tissue as a preliminary to injection of the agent. The needle assembly as described further facilitates bilateral injection of the sclerosing agent and minimizes the components and steps required in carrying out the procedure. It is to be understood that various modifications and changes may be made in the method and apparatus of the present invention without departing from the spirit and scope thereof as defined by the appended claims and reasonable equivalents thereof.

What is claimed is:

1. The method of transcervical sterilization of females comprising the steps of:
    (a) blindly inserting a plurality of needles into the uterus for a distance to penetrate the body tissue at one of the cornul portions on one side of the uterus;
    (b) injecting a sclerosing agent composed of paraformaldehyde in an alcohol solution through the needles into the body tissue from a point externally of the uterus in a concentration sufficient to occlude the cornul portion on the one side of the uterus;
    (c) withdrawing the needles from the tissue and relocating them in the body tissue of the opposite cornul portion and injecting a predetermined amount of said sclerosing agent therethrough and into the body tissue at that point; and
    (d) withdrawing the needles from the uterus.

2. The method according to claim 1 in which a plurality of needles are simultaneously advanced through a common needle guide into the body tissue at each of the cornul portions.

3. The method according to claim 1 in which a plurality of needles are successively advanced through a common needle guide for penetration of the body tissue at each of the cornul portions.

* * * * *